United States Patent [19]
Aragon et al.

[11] Patent Number: 5,112,314
[45] Date of Patent: May 12, 1992

[54] HYPODERMIC NEEDLE RECAPPING DEVICE

[76] Inventors: Steven B. Aragon, 6229 S. Iola Way; James W. Heller, 6190 S. Jamaica Ct., both of Englewood, Colo. 80111

[21] Appl. No.: 685,446

[22] Filed: Apr. 15, 1991

[51] Int. Cl.⁵ .............................. A61M 5/32
[52] U.S. Cl. .................................. 604/192
[58] Field of Search .............. 604/192, 187, 263; 206/365, 366

[56] References Cited

U.S. PATENT DOCUMENTS

| | | | |
|---|---|---|---|
| 4,596,562 | 6/1986 | Vernon | 604/192 |
| 4,717,386 | 1/1988 | Simmons | 604/192 |
| 4,737,149 | 4/1988 | Gillilan | 604/192 |
| 4,742,910 | 5/1988 | Staebler | 206/365 |
| 4,850,976 | 7/1989 | Heinrich | 604/192 |
| 4,892,522 | 1/1990 | Suzuki et al. | 604/192 |
| 4,900,309 | 2/1990 | Netherton | 604/192 |
| 4,906,235 | 3/1990 | Roberts | 604/192 |
| 4,919,656 | 4/1990 | Bracker et al. | 604/192 |
| 4,938,514 | 7/1990 | D'Addezio | 294/16 |

*Primary Examiner*—John D. Yasko
*Attorney, Agent, or Firm*—John E. Reilly

[57] ABSTRACT

A hypodermic needle recapping device is of one-piece construction and comprises a handle in the form of a thin, flat plate provided with a plurality of holes of different sizes for interchangeable use in recapping a needle, each hole being of a slightly larger size than the cap to be replaced on the needle, and a plurality of notches of different sizes on outer edges of the plate are used interchangeably for recapping different sized caps onto a needle.

12 Claims, 1 Drawing Sheet

HYPODERMIC NEEDLE RECAPPING DEVICE

This invention relates to needle guards for medical use; and more particularly relates to a novel and improved device for replacing the protective cap on a hypodermic needle.

BACKGROUND AND FIELD OF INVENTION

Hypodermic needles are used extensively in the fields of medicine, dentistry, surgery and veterinary medicine for the purpose of injecting or withdrawing fluids into or from blood vessels, subcutaneous tissue and other body spaces or cavities. The needle proper is characterized by being of elongated extremely slender tubular construction having a sharp end and an opposite connecting end for releasable connection to a syringe, cartridge or flexible tubing and the like. When not in use, the needle proper is covered by a protective cap in order to prevent accidental injury or contamination.

For the most part, needles are intended for one-time use although there are situations where the needle must be injected more than once into the same patient. For example, it is common for an anethesiologist to make several injections of the same drug into an intravenous access port during a surgical procedure. Dentists and surgeons often reinject a local anesthetic several times during the course of a procedure. Between injections, it is imperative that the protective cap or cover be replaced on the sharp end of the needle in order to protect the clinician from accidental puncture wounds from the needle point as well as to prevent inadvertent contact of the needle with non-sterile surfaces.

The process of recapping a needle is inherently dangerous and poses a significant risk to the clinician. The cap is not much larger in diameter than the needle point itself and in the past it has not been uncommon for the needle point to miss the cap opening and puncture the clinician's hand. This can cause infection of the clinician with the patient's disease and, for example, hepatitis and AIDS can be transmitted in this manner. The risk is so high that several private and governmental organizations have issued policies which either prohibit recapping of a needle or limit its use to situations where some other protective device is employed.

Numerous protective devices have been proposed for use in recapping a needle. Tweezers and hemostats have been used to hold the cap while the needle is reinserted. Although such instruments effectively keep the clinician's hand away from the cap, they are relatively expensive and cumbersome and have not been in widespread use. The cap can also be laid on a horizontal surface, such as, a counter or tray and scooped up with the needle. This requires even greater coordination and requires a second step in which the cap is securely pressed in place. In U.S. Pat. No. 4,596,562 to J. T. Vernon, a handle is provided with a series of different sized openings in which a cap can be inserted, the openings being dimensioned to grippingly engage the cover or cap. The handle requires a pair of spaced plates and a slotted end to receive a cover. However, loading of the cap into the plate requires time and a degree of manual dexterity. U.S. Pat. No. 4,938,514 to S. A. D'Addezio also employs a platelike hand tool having an opening for releasable insertion of a cap for protecting a needle. Here the opening size is regulated by a scissors-like handle and again the cap is grippingly engaged in the opening. U.S. Pat. Nos. 4,717,386 to J. Simmons and 4,919,656 to J. Bracker et al also employ plate-like handles with some form of a gripping means for engaging the cap to protect the user from pricking in the course of recapping the needle. Other representative patents of interest in this field are Letters U.S. Pat. Nos. 4,737,149 to T. A. Gillilan, 4,742,910 to C. R. Staebler, 4,850,976 to W. P. Heinrich et al, 4,892,522 to T. Suzuki et al, 4,900,309 to F. Netherton et al and 4,906,235 to C. W. Roberts.

In accordance with the present invention, it is proposed to overcome a number of drawbacks and disadvantages of prior art recapping devices in providing a low-cost, compact recapping device which is conformable for use with virtually any type or size of needle and cap and which reduces the number of steps and degree of manual dexterity required for handling and recapping of the needle, and can be used for uncapping as well.

In this regard, it is important that the device be sufficiently compact as to conveniently fit in the hand and can be placed on most instrument trays or can be carried by the clinician so as to be readily available for use when needed.

SUMMARY OF INVENTION

It is therefore an object of the present invention to provide for a novel and improved device for recapping hypodermic needles which is highly simplified, low-cost and is reliable and highly efficient to use.

Another object of the present invention is to provide for a novel and improved hypodermic needle recapping device which is conformable for use with various sizes and types of needles and caps and requires a minimum of manual dexterity to use in handling and recapping a needle and in such a way as to keep the clinician's hands or body away from the needle so as to avoid accidental injury or the transmission of disease.

A further object of the present invention is to provide for a hypodermic needle recapping device which is comprised of a single member having no moving parts and which member can be easily picked up and grasped and in which the cap itself may be engaged by the device for recapping without direct engagement or contact by the hand or fingers with the cap itself.

In accordance with the present invention, a hypodermic needle recapping device comprises an elongated body member having opposite ends, at least one generally circular aperture or hole extending through the thickness of the body member adjacent to one of the ends, the aperture being of a size larger than the diameter of a needle cap but smaller than the diameter of the cap shoulder, and at least one notch formed in an outer edge of the body adjacent to the aperture having an arcuate edge to at least partially surround the cap in order to press it against a fixed surface when the cap is resting on the surface whereby to facilitate insertion of a needle into an open end of the cap by grasping the body member in one's hand and holding the body member on edge with the notch pressed downwardly against the cap. In the alternative, the cap may be inserted through an aperture and the body member held on edge while the needle is inserted into the open end of the cap.

The body member is preferably in the form of a thin flat plate with a pair of apertures, there being one aperture at each end of the plate, and a pair of notches with one notch being located at each end of the plate, the apertures and notches being for interchangeable use in recapping different sized caps.

The above and other objects, advantages and features of the present invention will become more readily understood and appreciated from a consideration of the following detailed description of a preferred embodiment thereof when taken together with the accompanying drawings, in which:

DETAILED DESCRIPTION OF THE PREFERRED EMBODIMENT

Figure 1:
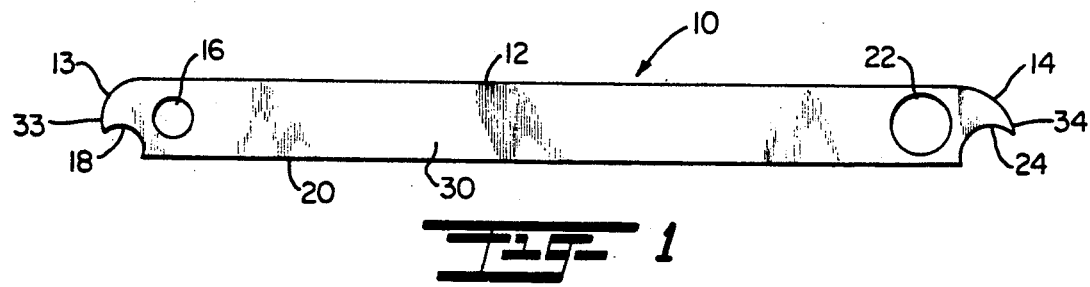
FIG. 1 is a front view in elevation of a preferred form of recapping device in accordance with the present invention.
Figure 2:
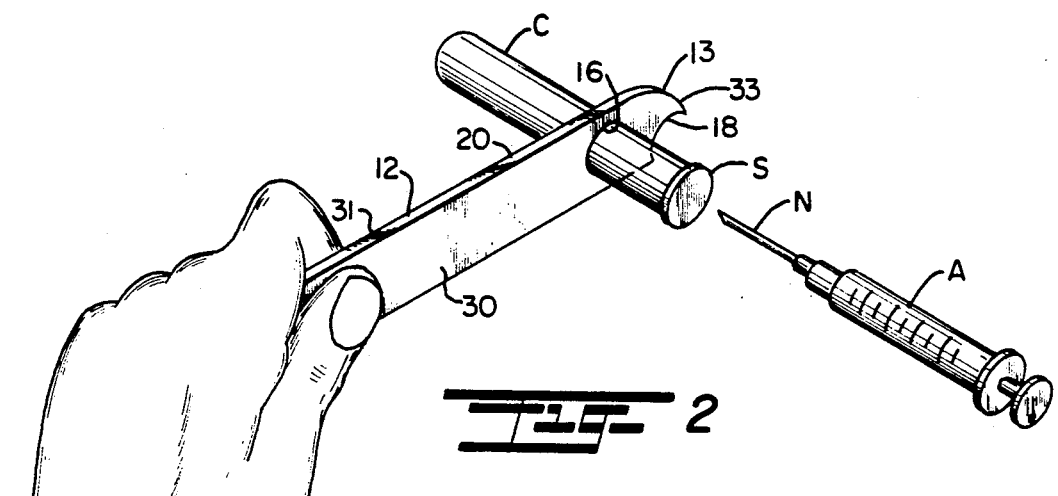
FIG. 2 is a somewhat perspective view illustrating the use of the preferred form of invention for insertion of a needle into a cap held in the device.
Figure 3:
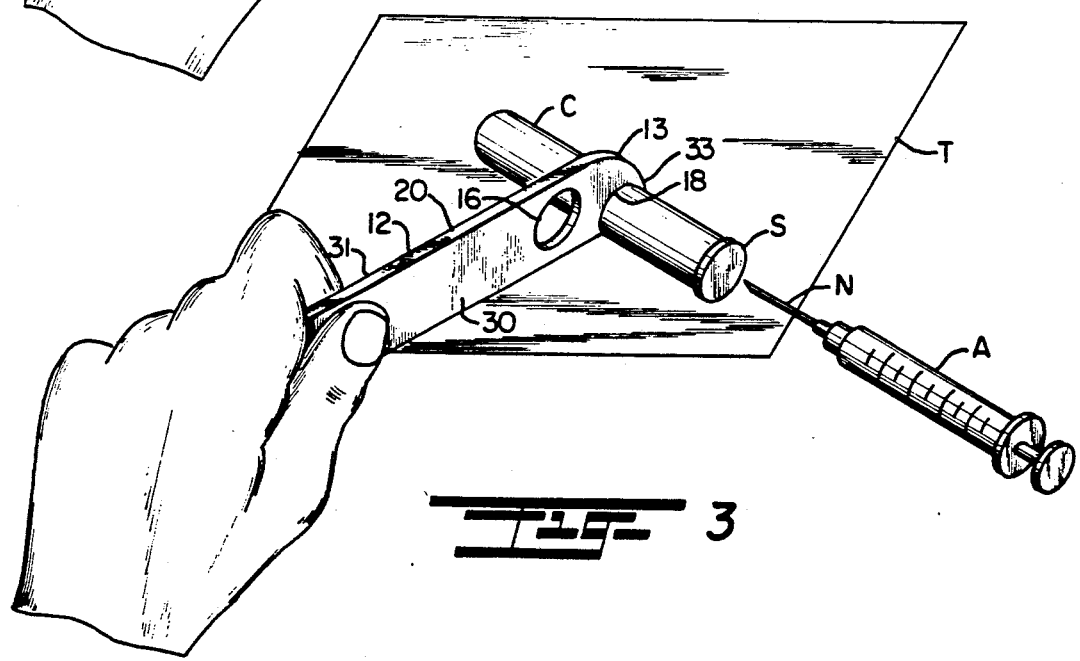
FIG. 3 is another perspective view illustrating the use of the invention in cooperation with a horizontal surface in recapping a needle.

Referring in detail to the drawings, there is illustrated in FIGS. 1 to 3 a preferred form of hypodermic needle recapping device 10 which is in the form of an elongated, thin flat plate or body 12 having opposite rounded ends 13 and 14. The end portion 13 is provided with a relatively small, circular aperture 16, and an arcuate notch 18 is formed at the juncture of the rounded end 13 and a straight edge 20 of the body 12. In turn, a relatively large circular aperture 22 is formed adjacent to the opposite end 14 and an arcuate notch 24 is formed at the juncture of the rounded end 14 with the straight edge 20. The radius of curvature of each notch 18 and 24 substantially corresponds to the radius of each respective aperture 16 and 22.

Preferably, the plate 12 has opposed flat surfaces 30 and 31 in parallel relation to one another, the straight edges 20 extending along opposite sides of the plate 12 and the rounded ends 13 and 14 are provided with generally circular edges 33 and 34 merging into the straight edges 20. For the purpose of illustration and not limitation, the body member 12 may have a length on the order of 6" and a width of 0.54'. The radius of curvature of each of the aperture 16 and notch 18 is on the order of 0.13", and the radius of curvature of each of the aperture 22 and notch 24 is on the order 0.193". The thickness of the body is uniform throughout and on the order of 0.075". Thus, the entire device is made of a single piece and may be suitably composed of a stainless steel material or plastic material which can be sterilized and reused a number of times, although sterilization is not necessarily required after each use.

As constructed, the device can be used in different modes: For instance, in a first mode as illustrated in FIG. 2, a needle cap C is loosely inserted into one of the apertures 16 and 22, depending upon the diameter of the cap. In the preferred form, the small opening 16 is sized for syringe-type needle assemblies and the larger opening 22 sized for cartridge-type needle assemblies. The cap may be inserted until the cap shoulder S rests against the surrounding edge of the opening and the device grasped in one hand, as shown, adjacent to the opposite end so that the hand is removed from any proximity to the cap itself. A needle N of a syringe-style needle assembly A is then inserted into the cap.

In a second, horizontal surface mode, as illustrated in FIG. 3, the cap C is placed on a horizontal surface, such as, a tabletop or tray as generally designated as T. One of the notches 18 or 24 is placed over the cap with a slight downward pressure sufficient to retain the cap in a stationary position on the tray. Again, the handle 12 is grasped toward the opposite end of the device to the notched portion used to engage the cap. In FIG. 3, the smaller notched area 18 is used for syringe-type needle assemblies while the larger notched portion 24 is employed for cartridge-type needle assemblies. Further, by locating the notched ends toward the rounded ends 13 or 14 of the device greatly facilitates handling and positioning of the cap in one of the notches for insertion of a needle into the cap, the needle being designated at N for a needle assembly A.

From the foregoing, it will be apparent that while a preferred form of recapping device has been illustrated and described, various modifications and changes may be made therein. For example, the notches may be located at different positions along the length of a handle and may be varied in size from the radii of the openings 16 and 22. Furthermore, different sized openings may be provided at either or both ends 13 and 14, although it has been found generally that two different sized apertures or holes are sufficient, particularly when provided in combination with different sized notches to retain the different sizes and dimensions of caps encountered in practice.

It is therefore to be understood that while a preferred form of invention is hereinbefore set forth and described, various other modifications and changes may be made in the construction and arrangement of parts as well as composition of materials without departing from the spirit and scope of the present invention as defined by the appended claims and reasonable equivalents thereof.

We claim:

1. A needle recapping device for replacing a cap on a hypodermic needle comprising:
    an elongated body member having opposite rounded ends;
    at least one generally circular aperture extending through the thickness of said body member adjacent to one of said opposite rounded ends, said aperture being of a size larger than the diameter of said cap; and p1 at least one notch in the form of a generally semi-circular opening extending through the thickness of said body member in an outer edge of said body member adjacent to said one of said rounded ends to at least partially surround said cap and press it against a surface when said cap is resting on said surface in order to facilitate insertion of a needle into an open end of said cap by grasping said body member in one's hand and holding said body member on edge with said notch downwardly against said cap.

2. A needled recapping device according to claim 1, said body member being a thin flat plate with said aperture extending through said thin dimension.

3. A needle recapping device according to claim 2, said plate having apertures of different size adjacent to said opposite rounded ends.

4. A needle recapping device according to claim 2, said plate having notches of different size of said opposite rounded ends.

5. A needle recapping device according to claim 1, said body member being a thin flat metal plate having opposed flat surfaces and straight edges along opposite sides and circular edges at said opposite rounded ends merging into said straight edges.

6. A needle recapping device according to claim 5, one of said notches located at the juncture of one of said circular edges and said straight edge.

7. A needle recapping device for replacing a cap on a hypodermic needle comprising:
   an elongated body member having opposite rounded ends;
   at least one generally circular aperture extending through the thickness of said body member adjacent to one of said opposite rounded ends, said aperture being of a size larger than the diameter of said cap; and
   notches of different sizes at said opposite said rounded ends, each said notch being of a size to at least partially surround a cap and press it against a surface when said cap is resting on said surface in order to facilitate insertion of a needle into an open end of said cap by grasping said body member in one's hand and holding said body member on edge with said notch pressed downwardly against said cap.

8. A needle recapping device for replacing a cap on a hypodermic needle comprising:
   an elongated body member having opposite rounded ends;
   at least one generally circular aperture extending through the thickness of said body member adjacent to one of said opposite rounded ends, said body member being a thin flat metal plate having opposed flat surfaces and straight edges along opposite sides and circular edges at opposite ends merging into said straight edges, said aperture being of a size larger than the diameter of said cap; and
   at least one notch formed in an outer edge of said body adjacent to said one of said rounded ends to at least partially surround said cap and press it against a surface when said cap is resting on said surface in order to facilitate insertion of a needle into an open end of said cap by grasping said body member in one's hand and holding said body member on edge with said notch pressed downwardly against said cap.

9. A needle recapping device according to claim 8, one of said notches located at the juncture of one of said circular edges and said straight edge.

10. A needle recapping device for replacing a cap on a hypodermic needle comprising:
    an elongated body member having opposite rounded ends; and
    notches of different size at said opposite rounded ends, each said notch being of a size to at least partially surround a cap and press it against a surface when said cap is resting on said surface in order to facilitate insertion of a needle into an open end of said cap by grasping said body member in one's hand and holding said body member on edge with said notch pressed downwardly against said cap.

11. A device according to claim 10, said notch being in the form of a generally semi-circular opening extending through the thickness of said body member.

12. A device according to claim 10, each said notch having a radius of curvature greater than that of the cap to be engaged.

* * * * *

UNITED STATES PATENT AND TRADEMARK OFFICE
CERTIFICATE OF CORRECTION

PATENT NO. : 5,112,314
DATED : May 12, 1992
INVENTOR(S) : Steven B. Aragon and James W. Heller It is certified that error appears in the above-identified patent and that said Letters Patent is hereby corrected as shown below:

| Column No. | Line No. | |
|---|---|---|
| 3 | 42 | cancel "0.54'" and substitute -- 0.54" -- |

IN THE CLAIMS:

Claim 1:

| | | |
|---|---|---|
| 4 | 44 | cancel "pl" |

Claim 2:

| | | |
|---|---|---|
| 4 | 55 | cancel "needled" and substitute -- needle -- |

Claim 4:

| | | |
|---|---|---|
| 4 | 62 | cancel "of" (second occurrence) and substitute -- at -- |

Signed and Sealed this

Third Day of August, 1993

Attest:

MICHAEL K. KIRK

*Attesting Officer*  *Acting Commissioner of Patents and Trademarks*